(12) United States Patent
Kim et al.

(10) Patent No.: US 8,173,404 B1
(45) Date of Patent: May 8, 2012

(54) PROCESS FOR CONVERTING WHOLE BARLEY INTO FERMENTABLE SUGARS

(75) Inventors: Tae Hyun Kim, Ames, IA (US); Kevin Hicks, Malvern, PA (US); Frank Taylor, Willow Grove, PA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 318 days.

(21) Appl. No.: 12/381,890

(22) Filed: Mar. 17, 2009

Related U.S. Application Data (60) Provisional application No. 61/072,883, filed on Apr. 3, 2008, provisional application No. 61/044,238, filed on Apr. 11, 2008.

(51) Int. Cl.
*C12P 7/58* (2006.01)

(52) U.S. Cl. ............. 435/137; 435/161; 435/96; 435/99

(58) Field of Classification Search .................. None
See application file for complete search history.

(56) References Cited

OTHER PUBLICATIONS

Palmarola-Adrados et al., Journal of Chemical Technology and Biotechnology, 2005, vol. 80, p. 85-91.*
Yu et al., J Agric. Food Chem., 2001, vol. 49, p. 4352-4358.*
Saha et al., Applied Biochemistry and Biotechnology, 1999, vol. 76, p. 65-77.*
J. Lora, et al., "Delignification of hardwoods by Autohydrolysis and Extraction", Tappi Press, vol. 61, (6), pp. 47-50, Jun. 1978.
L. Casebier, et al., "Chemistry and Mechanism of Water Prehydrolysis on Southern Pine Wood", Tappi Press, vol. 52, (12), pp. 2369-2377, Dec. 1969.
K. Grohmann, et al., "Optimization of Dilute Acid Prereatment of Biomass", Biotech. And Bioeng. Symp., (15), pp. 59-80, 1985.
H. Grethlein, "The Effect of Pore Size Distribution on the Rate of Enzymatic Hydrolysis of Cellulosic Substrates", Bio/Technology, pp. 155-160, Feb. 1985.
D.S. Burns, et al., "Surface Area of Pretreated Lignocellulosics as a Function of the Extent of Enzymatic Hydrolysis", Applied Biochemistry and Biotechnology, vol. 20/21, pp. 79-94, 1989.
E. Hockett, "Barley", Handbook of Cereal Science and Technology, vol. 99, pp. 81-125, 2000.
K. Grohmann, et al., "Dilute Acid Pretreatment Research", Solar Energy Research Institute, pp. 121-137, Jul. 1986.
A. Gibreel, et al., "Fermentation of Barley by Using *Saccharomyces cerevisiae*: Examination of Barley as a Feedstock for Bioethanol Production and Value-Added Products", Applied and Environmental Microbiology, vol. 75, (5), pp. 1363-1372, Mar. 2009.
J. Kim, et al., "Cellulose Hydrolysis Under Extremely Low Sulfuric Acid and High-Temperature Conditions", Applied Biochemistry and Biotechnology, vol. 91-93, pp. 331-340. 2001.
W. Mok, et al., "Productive and Parasitic Pathways in Dilute Acid-Catalyzed Hydrolysis of Cellulose", Ind. Eng. Chem. Res., vol. 31, pp. 94-100, 1992.
J Fernandez-Bolanos, et al., "Characterization of the Lignin Obtained by Alkaline Delignification and of the Cellulose Residue from Steam-Exploded Olive Stones", Bioresource Technology, vol. 68, pp. 121-132, 1999.
S. Allen, et al. "A Comparison of Aqueous and Dilute-Acid Siingle-Temperature Pretreatment of Yellow Poplar Sawdust", Ind. Eng. Chem. Res., vol. 40, pp. 2352-2361, 2001.
Y. Sun, et al., Dilute Acid Pretreatment of Rye Straw and Bermudagrass for Ethanol Production, Bioresource Technology, vol. 96, pp. 1599-1606, 2005.
Q. Nguyen, et al., "Two-Stage Dilute-Acid Pretreatment of Softwoods", Applied Biochemistry and Biotechnology, vol. 84-86, pp. 561-575, 2000.
B. Saha, et al., "Dilute Acid Pretreatment, Enzymatic Saccharification and Fermentation of Wheat Straw to Ethanol", Process Biochemistry, vol. 40, pp. 3693-3700, 2005.
A. Sluiter, et al., "Determination of Structural Carbohydrates and Lignin in Biomass" National Renewable Energy Laboratory, Technical Report NREL/TP-510-42618, 2008.

* cited by examiner

*Primary Examiner* — Kade Ariani
(74) *Attorney, Agent, or Firm* — John D. Fado; G. Byron Stover (57) ABSTRACT

A process for obtaining fermentable sugars from barley, involving treating hulled barley with $H_2SO_4$ to produce acid treated barley and treating the acid treated barley with enzymes to produce fermentable sugars.

21 Claims, 6 Drawing Sheets
(4 of 6 Drawing Sheet(s) Filed in Color)

130ºC 1.0% H₂SO₄ treated barley at 0h of enzyme hydrolysis at 96h of enzyme hydrolysis 10ºC 1.0% H₂SO₄ treated barley at 0h of enzyme hydrolysis at 96h of enzyme hydrolysis

Figure 6

PROCESS FOR CONVERTING WHOLE BARLEY INTO FERMENTABLE SUGARS

REFERENCE TO RELATED APPLICATION

This application claims the benefit of U.S. Provisional Application No. 61/072,883, filed 3 Apr. 2008, and 61/044,238, filed on 11 Apr. 2008, which are incorporated herein by reference in their entirety.

BACKGROUND OF THE INVENTION

The present invention relates to a process for obtaining fermentable sugars from whole barley, involving treating hulled barley with $H_2SO_4$ to produce acid treated barley and treating the acid treated barley with enzymes to produce fermentable sugars.

Barley is currently being used for ethanol production in Europe. Barley has some advantages as a corn substitute for ethanol production outside the Corn Belt in the U.S., particularly on the East Coast, the upper Midwest, and the Northwest (U.S. Department of Agriculture-National Agricultural Statistics Service (USDA-NASS), 2006, Crop Acreage and Yield US Maps Showing Counties Crop Year 2005 United States, <http://www.nass.usda.gov/Charts_and_Maps/Crops_County/index.asp> (accessed April, 2008)). North America grows approximately 14% of the world annual production of barley (Kim, S., and B. E. Dale, Biomass & Bioenergy, 26(4): 361-375 (2004)). Most fuel ethanol in the U.S. is corn-based. Hence most production facilities are located in the Corn Belt and not on either of the coasts where demand for ethanol is high (Hsu, T. A., Pretreatment of biomass, In: Wyman, C. E. (Ed.), Handbook on Bioethanol: Production and Utilization, 1996, Taylor & Francis Inc, Bristol, Pa., pp. 179-212).

Agronomically, winter barley fits extremely well into a three-crop two-year rotation with corn and soybeans. Barley grows well in areas where corn does not, and so might become a financially cost-effective source of fermentable sugars (e.g., ethanol feedstock) for those regions (Welsh, J. P., et al., Developing Strategies for Spatially Variable Nitrogen Application in Cereals, Part 1: Winter Barley, Biosystems Engineering, Vol. 84(4), pages 481-494 (2003); USDA-NASS, 2006). However, there are major obstacles in the barley ethanol conversion process, including (1) difficulty of clean separation of hull (lignocellulose) from the endosperm which makes the downstream conversion process more complicated, (2) high viscosity of mash in the liquefaction step due to mixed linkage β-glucan polysaccharides, and (3) difficulty of the conversion of the lignocellulosic hull into ethanol. Thus there is a need for a new process for producing fermentable sugars from barley.

SUMMARY OF THE INVENTION

In accordance with the present invention there is provided a process for obtaining fermentable sugars from whole barley, involving treating hulled barley with $H_2SO_4$ to produce acid treated barley and treating the acid treated barley with enzymes to produce fermentable sugars.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

DETAILED DESCRIPTION OF THE INVENTION

The present invention concerns a process for obtaining fermentable sugars from barley, involving treating hulled barley with $H_2SO_4$ to produce acid treated barley and treating the acid treated barley with enzymes to produce fermentable sugars.

The invention concerns a chemo-thermo-enzymatic (CTE) treatment for conversion of both starch and non-starch (lignocellulosic and beta-glucan) polysaccharides in hulled barley into fermentable sugars (which can be used for fuel ethanol production) without any hull separation and grinding steps. This process surprisingly produces much more fermentable sugar (and therefore more ethanol) from hulled barley than the traditional ethanol process which only converts the starch portion of barley into fermentable sugars. Barley can be a much-needed feedstock for fuel ethanol production in corn deficit regions, but there are major obstacles in the traditional barley ethanol conversion process: (1) difficulty of clean separation of hull (lignocellulose) from the endosperm, (2) high viscosity of mash due to mixed linkage beta-glucan polysaccharides, and (3) low amount of fermentable sugars in barley, leading to low ethanol yields. The new process surprisingly solves these problems. Currently no one converts the lignocellulosic barley hull into ethanol because it is not economical to conduct this process in a conventional barley ethanol plant. The process of the present invention allows the production of "cellulosic ethanol" along with starch ethanol in the same facility which is the ultimate goal of present day biorefineries: Optimum treatment conditions of CTE treatment for maximum fermentable sugars yield using flow through column reactor were found to be 5 mL/min of 1.0 wt % sulfuric acid, 110° C., 30 min and 4 mL 1% $H_2SO_4$ per g of barley of liquid throughput; one could utilize a batch reactor or a flow through reactor where the flow rate would dictate the time the barley is being reacted, for example 30 minutes. At these conditions about 100% of fermentable sugars were recovered as monomeric forms. Treatment at 110° C. retained most of the starch and protein in the solid (undissolved) portion which is critical for subsequent production of ethanol and high protein DDGS (Distiller's Dried Grains with Solubles). The acid pretreatment step also reduces viscosity from beta-glucans which will reduce the amount of beta-glucanase enzymes and cost required for the process.

The demand for fuel ethanol in the U.S. is drastically increasing due to the Energy Security and Independence Act of 2007 which calls for 36 billion gallons of conventional and advanced biofuels by 2022. To date, most of fuel ethanol in the U.S. is produced from corn and this is apparently causing major negative impacts on food and feed markets. Therefore, it is critical that we find substitutes for corn for the production of ethanol, especially outside the Corn Belt. Barley is such a grain, but its low starch content leads to low ethanol yields. Our new process surprisingly increases ethanol yields from barley, making it a much more economical feedstock. Since 20-25% of barley kernels are non-starch polysaccharides, conversion of these into ethanol would lead to enhanced ethanol yields. Plus, the DDGS coproduct would have higher protein and lower fiber, ideal for higher value poultry and swine markets. Because barley ethanol plants are just now being planned for the United States, our new process could be incorporated into the initial design, obviating the need to retrofit conventional barley plants. It is estimated that approximately 2 billion gallons of ethanol could be produced in the U.S. in new barley ethanol plants. With a conservative selling price of approximately $1.75 per gallon for ethanol, this represents an industry with at least $3.5 billion in primary product sales alone. If the increased conversion of non-starch polysaccharides leads to only a 10% increase in ethanol yields, that would be another $350 million in revenue. Increased value of DDGS would also lead to significant revenue for ethanol producers.

The process of the present invention surprisingly converts simultaneously both lignocellulose and starch (starch and non-starch polysaccharides) in hulled barley into fermentable sugars without any hull separation and grinding steps. The process uses dilute sulfuric acid solutions because, without being bound by theory, the hydronium ion in the liquid phase attacks and hydrolyzes β-glucans in the cell walls of endosperm and the aleurone layer and also the hemicellulose in the hull. Hydrolysis of the hemicellulose and some removal of lignin at elevated temperature and pressure surprisingly brought about a pretreatment effect for the lignocellulosic portion of the barley. Another advantage of pretreatment was the surprising potential to lower the enzyme dosage, which is a significant cost factor, because, without being bound by theory, of its hydrolytic effect on cellulose, mixed linkage beta-glucans (beta-glucans), hemicellulose, and starch.

Generally, hulled barley (including the hull) was treated with about 0.01 to about 10 wt. % $H_2SO_4$ (e.g., 0.01-10 wt %; preferably about 0.1 to about 1 wt. % $H_2SO_4$ (e.g., 0.1-1 wt %)) for about 10 to about 120 minutes (e.g., 10-120 minutes; preferably about 20 to about 60 minutes (e.g., 20-60 minutes), more preferably about 20 to about 40 minutes (e.g., 20-40 minutes), most preferably about 30 minutes (e.g., 30 minutes)) at a temperature and pressure of about 80° C. and about 15 psia to about 170° C. and about 150 psia (e.g., 80° C.-170° C. and 15-150 psia; preferably about 110° C. and about 30 psia to about 130° C. and about 60 psia (e.g., 110° C.-130° C. and 30-60 psia), more preferably about 110° C. and about 30 psia (e.g., 110° C. and 30 psia)). Pretreated (acid treated) hulled barley can be easily hydrolyzed by enzyme cocktail without any de-hulling or mechanical fractionation process.

The acid treated barley was then treated with an enzyme cocktail in buffer (e.g., 0.05 M citrate buffer) at about pH 4.5 to about pH 5 (e.g., pH 4.5-5) for about 1 day to about 5 days (e.g., 1-5 days; preferably about 2 days to about 4 days (e.g., 2-4 days), more preferably about 2.5 days to about 3.5 days (e.g., 2.5-3.5 days), most preferably about 3 days (e.g., 3 days)) at a temperature of about 30° C. to about 80° C. (e.g., 30°-80° C.; preferably about 45° C. to about 60° C. (e.g., 45°-60° C.), more preferably about 50° C. to about 55° C. (e.g., 50°-55° C.), most preferably about 50° C. (e.g., 50° C.)). The enzyme cocktail generally contains α-amylase, glucoamylase, β-glucosidase, and cellulase; for example 0.1 mL α-amylase (e.g., Spezyme Fred, Genencor International Inc., with about 22,000 LU/ml where LU is Liquefon Units), 0.1 mL glucoamylase (e.g., Optidex L-300, Genencor International Inc., with about 332 GAU/ml where GAU is GlucoAmylase Unit), 0.1 mL β-glucosidase (e.g., Novozyme 188, Novo Inc., 750 CBU/mL where CBU means cellobiase units), and 0.25 mL cellulase (e.g., GC-220; Genencor, 45 FPU/mL where FPU means filter paper units) per 3 g of barley solids (see examples below regarding commercial enzymes which can be used); any similar enzyme with similar activity to the commercial enzymes described above would also work. No other enzymes are required though they may be utilized. No separation step was necessary before the acid treated barley was treated with the enzyme cocktail, though the acid treated barley was allowed to cool and the pH was adjusted so that the enzymes in the enzyme cocktail were not adversely affected. During enzyme hydrolysis, the acid treated hulled barley, including the hulls, was completely hydrolyzed into fermentable sugars.

The fermentable sugars can then be utilized, for example by conversion to ethanol or other fermentation-derived products using methods known in the art.

The process of the present invention can surprisingly simplify the current barley ethanol process by eliminating or substituting the de-hulling and other cooking processes. In the current barley ethanol facilities, the hull, lignocellulose, can be obtained as a byproduct with no additional cost because current barley ethanol producers do not utilize lignocellulose in their starch ethanol plant. The present invention is an economical process to enhance the current barley ethanol process by utilizing both starch and lignocellulose in a single step. Barley hull is approximately 7-11% of whole barley kernel based on weight; therefore utilization of hull for the ethanol production may add nearly 6-10% ethanol production increase.

Figure 2:
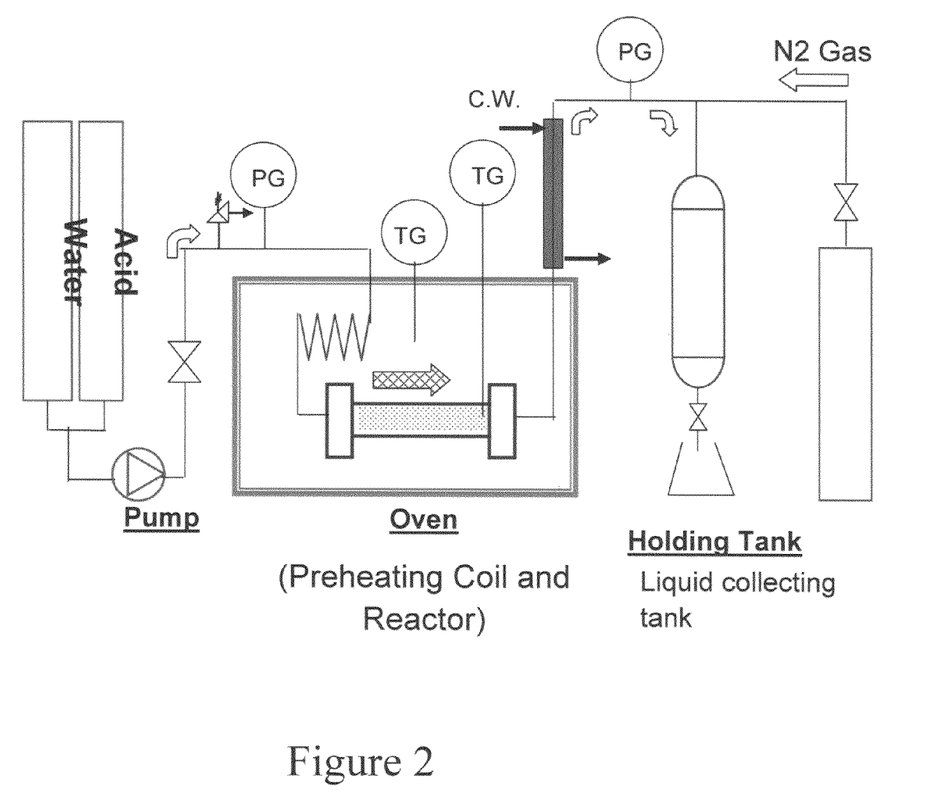
FIG. 2 shows a schematic diagram of a flow-through reactor system which can be utilized in the process of the present invention.

FIG. 2 shows a schematic diagram of a flow-through reactor system which can be utilized in the process of the present invention.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Both lignocellulosic and starch polysaccharides (starch and non-starch polysaccharides) in hulled barley were converted into fermentable sugars simultaneously without any hull separation and grinding steps. Pretreatment with dilute acid (e.g., sulfuric acid) at elevated temperature surprisingly improved the digestibility of the hull portion and also resolved the high viscosity problems due to beta-glucans that would impede the further processing and fermentation of the resulting sugars. Conversion of starch and cellulose into fermentable sugars was achieved by chemical pretreatment and hydrolysis with an enzyme cocktail. Production of ethanol from barley (endosperm+hull) was surprisingly improved by hydrolyzing β-glucan in the earlier stage since the β-glucan would be problematic in terms of high viscosity in the fermentor as noted above. Because the β-glucan was mainly present in the cell wall of endosperm and aleurone layer, the conditions for β-glucan removal could be optimized or minimized. In the latter process, recovered β-glucan in the liquor could be isolated and used as the dietary fiber, if it is still in its natural state.

Figure 1:
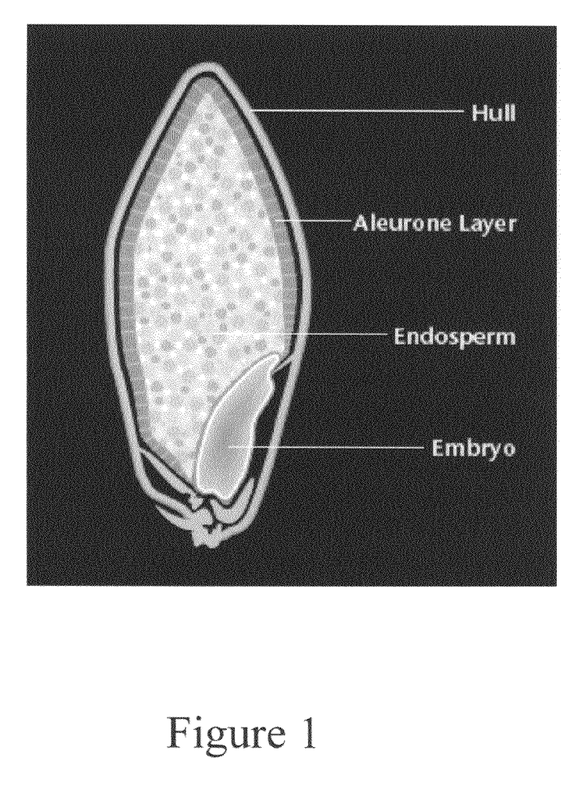
FIG. 1 shows a cross section of barley (from: An Importer's Guide to U.S. Barley, 2004, U.S. Grains Council (www.grains.org), Washington D.C.).

Materials: Nomini barley, a six-row winter barley (FIG. 1 shows a cross section of barley); table 1 describes the composition of whole barley. Cellulase enzyme, GC-220 (Genencor, Lot No. 301-04232-162, 45 FPU/mL). β-glucosidase, Novozyme 188 (Novo Inc., Lot No. 11K1088, 750 CBU/mL). Amylase (Spezyme Fred, Genencor International Inc. Lot# 107-02285-003, optimum conditions: pH 6.0, 80° C., 60 min). Glucoamylase (Optidex L-300, Genencor International Inc. Lot# 105-01232-001, optimum conditions: pH 4.5, 55° C., 60 min).

Pretreatment conditions: Whole hulled barley was treated at 110°-170° C., 30 min, 5 mL of 0.1-1.0 wt. % $H_2SO_4$, 300 psi in 70 mL of stainless steel flow-through column reactor (void %=50-60%).

Enzymatic hydrolysis conditions: 3% solid loading per 100 mL, 0.05 M Citrate buffer, 50° C., 150 rpm. α-amylase 0.1 mL, glucoamylase 0.1 mL, β-glucosidase 0.1 mL, cellulase 0.25 mL per 3 g (oven dry weight) of solid loading in 100 mL flask reactor.

Figure 3:
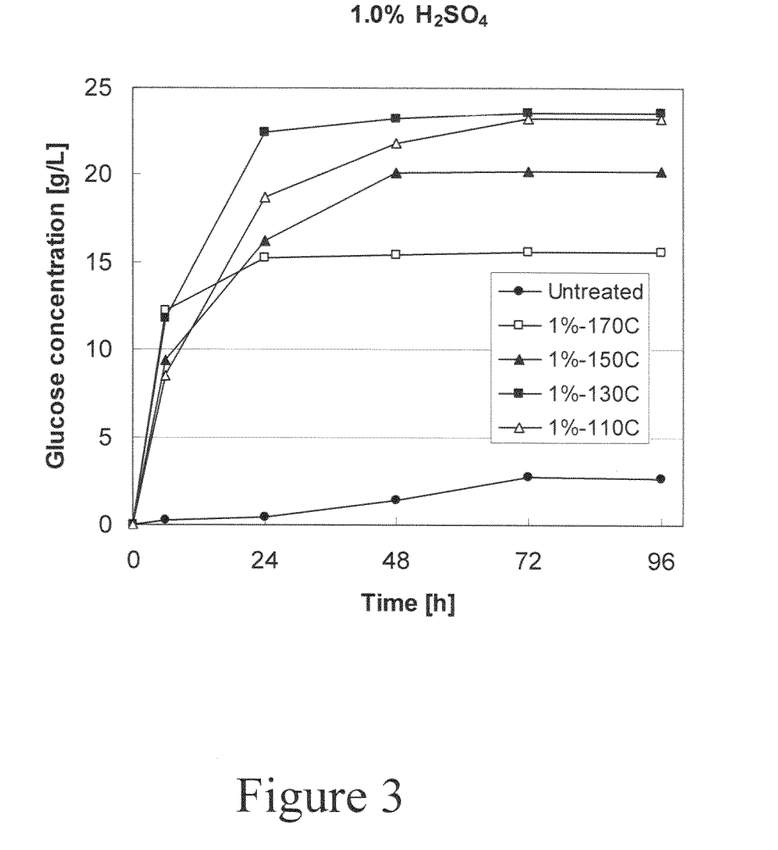
FIG. 3 shows glucose concentration profile in enzyme hydrolysis after pretreatment in 1% $H_2SO_4$ at different temperatures as described in the Examples below.

FIG. 3 shows the glucose concentration profile in enzymatic hydrolysis after pretreatment in 1% $H_2SO_4$ at different temperatures. The 24-hr rates of enzymatic hydrolysis at 110° C. and 130° C. were similar. At higher temperatures, the yield of glucose was reduced due to thermochemical hydrolysis and degradation of sugars. Enzymatic reactions were essentially complete after 48 hours.

Figure 4:
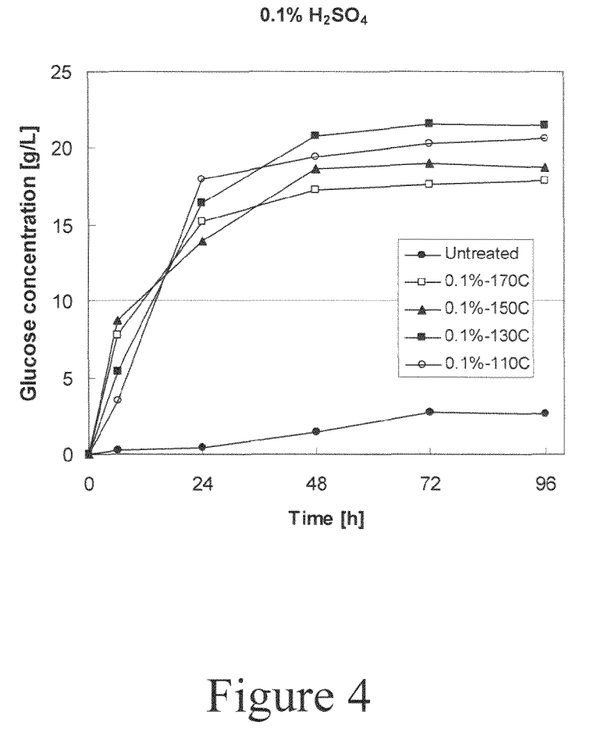
FIG. 4 shows glucose concentration profile in enzyme hydrolysis (0.1% $H_2SO_4$) after pretreatment in 0.1% $H_2SO_4$ as described in the Examples below.

FIG. 4 shows the glucose concentration profile in enzymatic hydrolysis after pretreatment in 0.1% $H_2SO_4$. The results were similar to those for 1% $H_2SO_4$ except that the final yield of glucose was reduced for all but the highest temperature.

Figure 5:
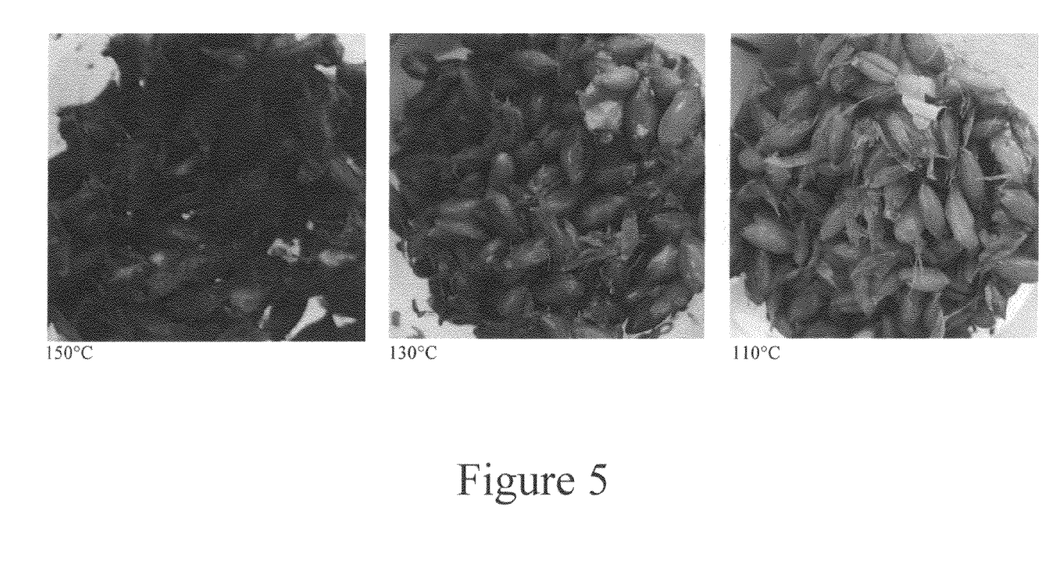
FIG. 5 shows pictures of hulled barley after acid pretreatment (1% $H_2SO_4$) as described in the Examples below. The picture on the left was pretreatment at 150° C.; the picture in the middle was pretreatment at 130° C.; and the picture on the right was pretreatment at 110° C.

FIG. 5 shows pictures of hulled barley after acid pretreatment (1% $H_2SO_4$). Darkening of the grain was more obvious at higher temperatures. Significant separation of the hulls was observed even at the lower temperature.

Figure 6:
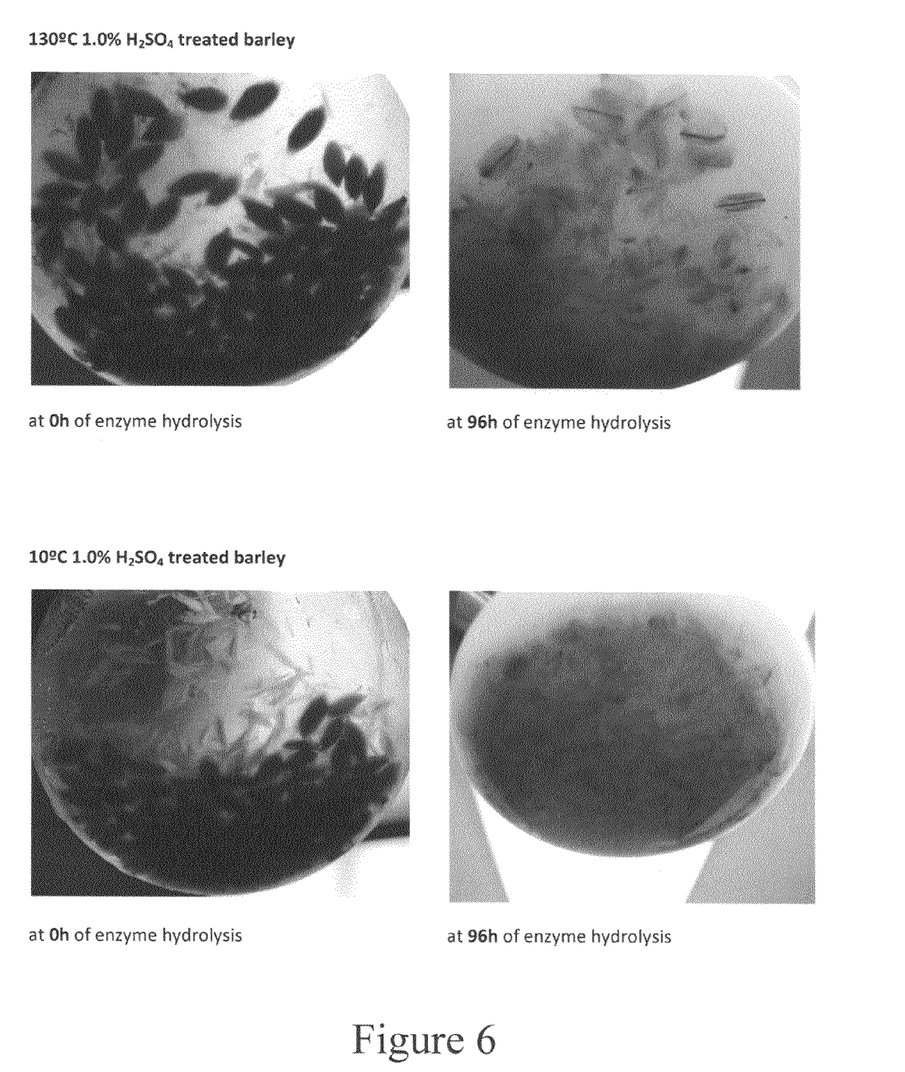
FIG. 6 shows pictures of hulled barley before and after enzymatic hydrolysis (1% $H_2SO_4$ pretreatment) as described in the Examples below. The picture on the top left was pretreatment at 0 hours of enzyme hydrolysis (130° C., 1.0% $H_2SO_4$ treated barley); the picture on the top right was pretreatment at 96 hours of enzyme hydrolysis (130° C., 1.0% $H_2SO_4$ treated barley); the picture on the bottom left was pretreatment at 0 hours of enzyme hydrolysis (110° C., 1.0% $H_2SO_4$ treated barley); and the picture on the bottom right was pretreatment at 96 hours of enzyme hydrolysis (110° C., 1.0% $H_2SO_4$ treated barley).

FIG. 6 shows pictures of hulled barley before and after enzymatic hydrolysis (1% $H_2SO_4$ pretreatment). The physical disintegration of the grain appeared more complete after enzymatic treatment of the barley pretreated at 110° C.

Table 2 shows the mass balance of components in hulled barley untreated or treated by the combined chemo-, thermo-, and enzymatic treatment. Untreated hulled barley was shown to contain 67.2% of fermentable sugars. This was determined by using the "Biomass Analysis Technology Team LAP (laboratory analytical procedure)" (NREL, 2004). In this process for converting lignocellulosic polysaccharides into fermentable sugars a multi-step process was used to make sure no sugars are lost. The data in Table 2 show that the present invention, under optimum conditions, was surprisingly capable of converting 100% of all polysaccharides (starch and non-starch) polysaccharides into fermentable sugars.

Summary: Pretreatment of hulled barley using sulfuric acid at elevated temperature and pressure followed by enzyme hydrolysis was surprisingly very effective in converting barley into fermentable sugars. Pretreated hulled barley can be easily hydrolyzed by an enzyme cocktail without any de-hulling or mechanical fractionation process, and probably pre- or post-fractionation of barley may increase the hydrolysis rate; after sulfuric acid treatment the hull can be easily removed even by hand. After enzyme hydrolysis, the treated hulled barley, including hull, was completely hydrolyzed into monomeric sugars. With proper operation, about 100% of fermentable sugars were recovered. Treatment at 110° C. retained most of starch and protein in the solids.

All of the references cited herein, including U.S. patents, are incorporated by reference in their entirety. Also incorporated by reference in their entirety are the following references: Palmarola-Adrados, B., et al., J. Chem. Technol. Biotech., 80(1): 85-91 (2005); Burns, D. S., et al., Appl. Biochem. Biotechnol., 24-25: 67-73 (1990); Grethlein, H., Bio/Technology, 3(2): 155-160 (1985); Jacobsen, S., and C. E. Wyman, Appl. Biochem. Biotechnol., 84-86: 81-96 (2000); Kim, J. S., et al., Appl. Biochem. Biotechnol., 91-93: 331-340 (2001); Mok, W. S. L., et al., Ind. Eng. Chem. Res., 31: 1, 94-100 (1992); AOAC (Association of Official Agricultural Chemists) Method 996.11, AACC (American Association for Clinical Chemistry) Method 76.13, ICC Standard Method No. 168 (Megazyme Total Starch Assay Procedure) (Amyloglucosidase/α-Amylase method) K-TSTA 05/06; NREL (National Renewable Energy Laboratory, Golden, Colo.), 2004, "Procedure Title: Determination of Structural Carbohydrates and Lignin in Biomass Version" in the LAP (Laboratory Analytical Procedure), LAP-002, 003, 004, 017, and 019, Primary author Amie Sluiter, www1.eere.energy-.gov/biomass/analytical_procedures.html.

Thus, in view of the above, the present invention concerns (in part) the following:

A process (for obtaining fermentable sugars from barley), comprising (or consisting essentially of or consisting of) treating hulled barley with $H_2SO_4$ to produce acid treated barley and treating said acid treated barley with enzymes to produce fermentable sugars.

The above process, wherein said process comprises (or consists essentially of or consists of) treating hulled barley with about 0.01 to about 10 wt. % $H_2SO_4$ for about 10 to about 120 minutes at a temperature of about 80° C. to about 170° C.

The above process, wherein said hulled barley is treated with about 0.01 to about 10 wt. % $H_2SO_4$. The above process, wherein said hulled barley is treated with about 0.1 to about 1 wt. % $H_2SO_4$. The above process, wherein said hulled barley is treated with $H_2SO_4$ for about 10 to about 120 minutes.

The above process, wherein said hulled barley is treated with $H_2SO_4$ for about 20 to about 60 minutes. The above process, wherein said hulled barley is treated with for about 20 to about 40 minutes. The above process, wherein said hulled barley is treated with $H_2SO_4$ for about 30 minutes.

The above process according to claim 1, wherein said hulled barley is treated with $H_2SO_4$ at a temperature of about 80° C. to about 170° C.

The above process according to claim 1, wherein said hulled barley is treated with $H_2SO_4$ at a temperature of about 110° C. to about 130° C.

The above process, wherein said hulled barley is treated with $H_2SO_4$ at a temperature of about 110° C.

The above process, wherein said hulled barley is treated with $H_2SO_4$ at a pressure of about 15 psia to about 150 psia. The above process, wherein said hulled barley is treated with $H_2SO_4$ at a pressure of about 30 psia to about 60 psia. The above process, wherein said hulled barley is treated with $H_2SO_4$ at a pressure of about 30 psia.

The above process, wherein said hulled barley is treated with $H_2SO_4$ at a temperature of about 80° C. to about 170° C. and at a pressure of about 15 psia to about 150 psia.

The above process, wherein said hulled barley is treated with $H_2SO_4$ at a temperature of about 110° C. to about 130° C. and at a pressure of about 30 psia to about 60 psia.

The above process, wherein said hulled barley is treated with $H_2SO_4$ at a temperature of about 110° C. and at a pressure of about 30 psia.

The above process, wherein said process comprises (or consists essentially of or consists of) treating said acid treated barley with enzymes at about pH 4.5 to about pH 5 for about 1 day to about 5 days at a temperature of about 30° C. to about 80° C. to produce fermentable sugars.

The above process, wherein said acid treated barley is treated with enzymes at a pH of about pH 4.5 to about pH 5.

The above process, wherein said acid treated barley is treated with enzymes for about 1 day to about 5 days. The above process, wherein said acid treated barley is treated with enzymes for about 2 days to about 4 days. The above process, wherein said acid treated barley is treated with enzymes for about 2.5 days to about 3.5 days. The above process, wherein said acid treated barley is treated with enzymes for about 3 days.

The above process, wherein said acid treated barley is treated with enzymes at a temperature of about 30° C. to about 80° C. The above process, wherein said acid treated barley is treated with enzymes at a temperature of about 45° C. to about 60° C. The above process, wherein said acid treated barley is treated with enzymes at a temperature of about 50° C. to about 55° C. The above process, wherein said acid treated barley is treated with enzymes at a temperature of about 50° C.

The above process, wherein said enzymes are selected from the group consisting of α-amylase, glucoamylase, β-glucosidase, cellulase, and mixtures thereof.

The above process, wherein said enzymes are α-amylase, glucoamylase, β-glucosidase, and cellulase.

The above process, wherein said enzymes are α-amylase 0.1 mL, glucoamylase 0.1 mL, β-glucosidase 0.1 mL, and cellulase 0.25 mL per 3 g of barley solids.

The above process, wherein said process does not involve a hull separation step.

The above process, wherein said process does not involve a grinding step.

The above process, further comprising producing ethanol from said fermentable sugars.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

| Substrate (whole barley) Composition | |
|---|---|
| Components | Compositions (dry wt. %) |
| Starch* | 55.5 |
| Cellulose** | 4.0 |
| Xylan* | 3.7 |
| β-Glucan | 4.0 |
| Protein | 9.9 |
| Ash | 2.8 |
| Lignin* | 3.0 |
| Oil | 2.8 |
| Others | 14.3 |

*Total starch content was determined by AOAC/AACC method using Megazyme total starch assay kit (Megazyme International, Cat. # K-TSTA 05/06).
**Lignocellulose analysis was completed using method described in "Biomass Analysis Technology Team LAP (laboratory analytical procedure)" (NREL, 2004).

TABLE 2

Mass balance table of acid treated whole barley[1]

| | Solid | | | | | | | | | | Liquid[6] | | Total |
|---|---|---|---|---|---|---|---|---|---|---|---|---|---|
| | After pretreatment | | | | | | | Enzyme hydrolyzed sugars[3] | | | Monomer + Oligomer | | |
| Conditions | S.R.[2] [wt. %] | Starch [wt. %] | Cellulose (glucan)[4] [wt. %] | Xylan [wt. %] | β-Glucan [wt. %] | Proteins [wt. %] | Ash [w %] | Glucan [wt. %] | Xylan [wt %] | Total [wt. %] | Glucan [wt. %] | Xylan [wt. %] | (Sold Liquid) [wt. %] |
| Untreated | 100 | 55.3 | 4.0 | 3.7 | 4.0 | 9.9 | 2.8 | 8.1 | 0.0 | 8.1 | — | — | 67.0 |
| 1.0 wt. % $H_2SO_4$ | | | | | | | | | | | | | |
| 170 | 27.4 | 5.9 | N/A | 0.1 | N/A | 5.6 | 1.0 | 12.8 | 0.1 | 12.9 | 39.1 | 4.7 | 56.7 |
| 150 | 46.2 | 19.6 | N/A | 0.3 | N/A | 7.5 | 1.1 | 28.0 | 0.3 | 28.4 | 27.8 | 4.1 | 60.4 |
| 130 | 78.3 | 43.1 | N/A | 0.7 | N/A | 8.9 | 1.7 | 55.4 | 0.7 | 56.1 | 8.4 | 3.1 | 67.5 |
| 110 | 92.1 | 53.8 | N/A | 0.9 | N/A | 9.7 | 2.0 | 64.0 | 0.9 | 64.9 | 0.5 | 2.2 | 67.6 |
| 0.1 wt. % $H_2SO_4$ | | | | | | | | | | | | | |
| 170 | 35.5 | 12.0 | N/A | 0.2 | N/A | 6.0 | 0.9 | 19.1 | 0.2 | 19.3 | 34.5 | 5.0 | 58.8 |
| 150 | 53.9 | 21.7 | N/A | 0.4 | N/A | 8.1 | 1.1 | 30.3 | 0.4 | 30.7 | 25.4 | 3.1 | 59.3 |
| 130 | 83.3 | 43.7 | N/A | 0.6 | N/A | 9.4 | 1.7 | 53.8 | 0.6 | 54.4 | 6.5 | 1.2 | 62.1 |
| 110 | 97.3 | 54.1 | N/A | 0.6 | N/A | 9.6 | 2.0 | 60.1 | 0.6 | 60.7 | 0.5 | 0.2 | 61.4 |

[1] Data in the table based on the oven dry untreated whole bailey, including grain and hull. Whole hulled barley, including 12 wt. % hull was pretreated with sulfuric acid; pretreatment conditions 110°-170° C., 30 min, 5 mL/min of 0.1-1.0 wt. % $H_2SO_4$, 300 psi in a 70 mL stainless steel flow-through column reactor packed with hulled barley(void % = 50-60% ).
[2] S.R.: solid remaining after pretreatment
[3] Enzyme hydrolysis: α-amylase 0.1 mL, glucoamylase 0.1 mL, β-glucosidase 0.1 mL, cellulase 0.25 mL per 3 g of solid loading in 100 mL flask reactor; 50° C., 150 rpm, pH = 5, and 072 h in 0.05 M citrate buffer. These numbers were converted into potential producible sugars percentage using actual remaining solids, based on sugar yield from 3 g standard enzyme digestibility test.
[4] Cellulose portion wasnot measured de to small sample quantity
[5] Protein in liquid was negligible.
[6] Liquid was hydrolyzed in 4% sulfuric acid at 121° C. for 1 h.
[7] Data is sum of sugars from hydrolysate after enzyme hydrolysis andugars from collected liquid after secondary hydrolysis.

We claim:

1. A process for obtaining fermentable sugars from barley, comprising treating whole hulled barley with about 0.01 to about 10 wt. % $H_2SO_4$ for about 10 to about 120 minutes at a temperature of about 80° C. to about 170° C. to produce acid treated barley and treating said acid treated barley with enzymes to produce fermentable sugars; wherein said process does not involve a grinding step and wherein said process does not involve hull separation; wherein said enzymes are α-amylase, glucoamylase, β-glucosidase, and cellulase, thereby obtaining fermentable sugars from said barley.

2. The process according to claim 1, wherein said hulled barley is treated with about 0.1 to about 1 wt. % $H_2SO_4$.

3. The process according to claim 1, wherein said hulled barley is treated with $H_2SO_4$ for about 20 to about 60 minutes.

4. The process according to claim 1, wherein said hulled barley is treated with $H_2SO_4$ for about 20 to about 40 minutes.

5. The process according to claim 1, wherein said hulled barley is treated with $H_2SO_4$ for about 30 minutes.

6. The process according to claim 1, wherein said hulled barley is treated with $H_2SO_4$ at a temperature of about 80° C. to about 170° C. and at a pressure of about 15 psia to about 150 psia.

7. The process according to claim 1, wherein said process comprises treating said acid treated barley with enzymes at about pH 4.5 to about pH 5 for about 1 day, to about 5 days at a temperature of about 30° C. to about 80° C. to produce fermentable sugars.

8. The process according to claim 1, wherein said acid treated barley is treated with enzymes at a pH of about pH 4.5 to about pH 5.

9. The process according to claim 1, wherein said acid treated barley is treated with enzymes for about 1 day to about 5 days.

10. The process according to claim 1, wherein said acid treated barley is treated with enzymes for about 2 days to about 4 days.

11. The process according to claim 1, wherein said acid treated barley is treated with enzymes for about 2.5 days to about 3.5 days.

12. The process according to claim 1, wherein said acid treated barley is treated with enzymes for about 3 days.

13. The process according to claim 1, wherein said acid treated barley is treated with enzymes at a temperature of about 30° C. to about 80° C.

14. The process according to claim 1, wherein said acid treated barley is treated with enzymes at a temperature of about 45° C. to about 60° C.

15. The process according to claim 1, wherein said acid treated barley is treated with enzymes at a temperature of about 50° C. to about 55° C.

16. The process according to claim 1, wherein said acid treated barley is treated with enzymes at a temperature of about 50° C.

17. The process according to claim 1, further comprising producing ethanol from said fermentable sugars.

18. The process according to claim 1, wherein said hulled barley is treated with $H_2SO_4$ at a temperature of about 110° C. to about 130° C. and at a pressure of about 30 psia to about 60 psia.

19. The process according to claim 1, wherein said hulled barley is treated with $H_2SO_4$ at a temperature of about 110° C. and at a pressure about 30 psia.

20. The process according to claim 1, wherein said process consists essentially of treating whole hulled barley with about 0.01 to about 10 wt. % $H_2SO_4$ for about 10 to about 120 minutes at a temperature of about 80° C. to about 170° C. to produce acid treated barley and treating said acid treated barley with enzymes to produce fermentable sugars, and optionally producing ethanol from said fermentable sugars; wherein said process does not involve a grinding step and wherein said process does not involve hull separation; wherein said enzymes are α-amylase, glucoamylase, β-glucosidase, and cellulase, thereby obtaining fermentable sugars from said barley.

21. The process according to claim 1, wherein said process consists of treating whole hulled barley with about 0.01 to about 10 wt. % $H_2SO_4$ for about 10 to about 120 minutes at a temperature of about 80° C. to about 170° C. to produce acid treated barley and treating said acid treated barley with enzymes to produce fermentable sugars, and optionally producing ethanol from said fermentable sugars; wherein said process does not involve a grinding step and wherein said process does not involve hull separation; wherein said enzymes are α-amylase, glucoamylase, β-glucosidase, and cellulase, thereby obtaining fermentable sugars from said barley.

* * * * *